(12) United States Patent
Spears

(10) Patent No.: US 10,568,519 B1
(45) Date of Patent: Feb. 25, 2020

(54) TERAHERTZ SCANNING SYSTEM FOR AN INTRAVASCULAR SPACE

(71) Applicant: The Spectranetics Corporation, Colorado Springs, CO (US)

(72) Inventor: Matthew Spears, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 990 days.

(21) Appl. No.: 14/728,168

(22) Filed: Jun. 2, 2015

Related U.S. Application Data

(60) Provisional application No. 62/006,636, filed on Jun. 2, 2014.

(51) Int. Cl.
*A61B 5/00* (2006.01)
*A61B 18/24* (2006.01)
*A61B 18/00* (2006.01)

(52) U.S. Cl.
CPC .......... *A61B 5/0084* (2013.01); *A61B 5/0062* (2013.01); *A61B 18/245* (2013.01); *A61B 2018/00345* (2013.01); *A61B 2018/00577* (2013.01); *A61B 2018/00702* (2013.01)

(58) Field of Classification Search
CPC ..................................................... A61B 5/0084
See application file for complete search history.

(56) References Cited

U.S. PATENT DOCUMENTS

| | | | |
|---|---|---|---|
| 2009/0123111 A1* | 5/2009 | Udd ........................ | A61B 5/06 385/13 |
| 2014/0127707 A1* | 5/2014 | Ouchi ............... | G01N 21/3586 435/7.1 |

* cited by examiner

*Primary Examiner* — Rochelle D Turchen

(57) ABSTRACT

The present disclosure relates to a terahertz imaging system for imaging a lumen of a human, such as an intravascular space. A system may include a catheter and a terahertz transceiver device coupled to the catheter. The terahertz transceiver device may be operative to output terahertz radiation through a lumen of a human and to receive reflection signals based on the terahertz radiation. A power source may be coupled to the terahertz transceiver device. The system may further include a controller in communication with the terahertz transceiver device. The controller is operative to obtain an image of the lumen based on the reflection signals.

17 Claims, 3 Drawing Sheets ical Application Ser. No. 62/006,636, filed Jun. 2, 2014, entitled TERA-
HERTZ SCANNING SYSTEM FOR AN INTRAVASCULAR SPACE

TERAHERTZ SCANNING SYSTEM FOR AN INTRAVASCULAR SPACE

CROSS-REFERENCE TO RELATED APPLICATION

The present application claims the benefit of and priority to, under 35 U.S.C. § 119(e), U.S. Provisional Application Ser. No. 62/006,636, filed Jun. 2, 2014, entitled TERAHERTZ SCANNING SYSTEM FOR AN INTRAVASCULAR SPACE, which is hereby incorporated by reference in its entirety for all purposes.

FIELD OF THE DISCLOSURE

The present disclosure relates generally to imaging a target site of a human, and more specifically to a terahertz imaging catheter for imaging and scanning an intravascular space.

BACKGROUND

Imaging technology is used to provide visualizations of surgical areas in the human body including vascular spaces. Before performing angioplasty, for example, it is beneficial for doctors to know the extent of the disease. Limited knowledge of the state of the disease before intervening may lead to use of the incorrect device or method for treatment. Imaging technology is also used to visualize the vascular space during and/or after the angioplasty.

Several methods currently exist for visualizing vascular spaces and arterial lesions. Fluoroscopy uses real-time x-ray imaging in combination with contrast agents to visualize blood flow before performing angioplasty. However, the patient or doctor potentially may be exposed to high doses of radiation with x-ray imaging. Intravascular imaging technologies such as intravascular ultrasound (IVUS) and optical coherence tomography (OCT) provide visualizations of the interior of vascular spaces. For example, IVUS and OCT techniques both scan a two-dimensional (2D) cross section perpendicular to the artery. IVUS and OCT both require pulling the sensing device through a cleared lesion to obtain an image, and thus the doctor must first clear the lesion prior to using the device. None of the current solutions produce three-dimensional (3D) images that are capable of scanning the lesion prior to and during the intervention.

SUMMARY

According to an exemplary embodiment of the present disclosure, a terahertz imaging system is provided including a catheter and a terahertz transceiver device coupled to the catheter. The terahertz transceiver device is operative to output terahertz radiation from within or through a lumen of a human and to receive reflection signals based on the terahertz radiation. The terahertz imaging system further includes a power source coupled to the terahertz transceiver device and a controller in communication with the terahertz transceiver device. The controller is operative to obtain an image of the lumen based on the reflection signals.

According to another exemplary embodiment of the present disclosure, a terahertz imaging method includes providing a catheter, a terahertz transceiver device coupled to the catheter, and a power source; activating the power source to deliver terahertz radiation from the power source to the terahertz transceiver device; emitting the terahertz radiation from the terahertz transceiver device through a lumen of a human; receiving reflection signals based on the terahertz radiation; and obtaining an image of the lumen based on the reflection signals.

According to another exemplary embodiment of the present disclosure, a non-transitory computer-readable medium contains instructions that, when executed, cause one or more processors to perform a method that includes activating a power source to deliver terahertz radiation from the power source to a terahertz transceiver device coupled to a catheter; emitting the terahertz radiation from the terahertz transceiver device through a lumen of a human; receiving reflection signals based on the terahertz radiation; and obtaining an image of the lumen based on the reflection signals.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

Figure 1:
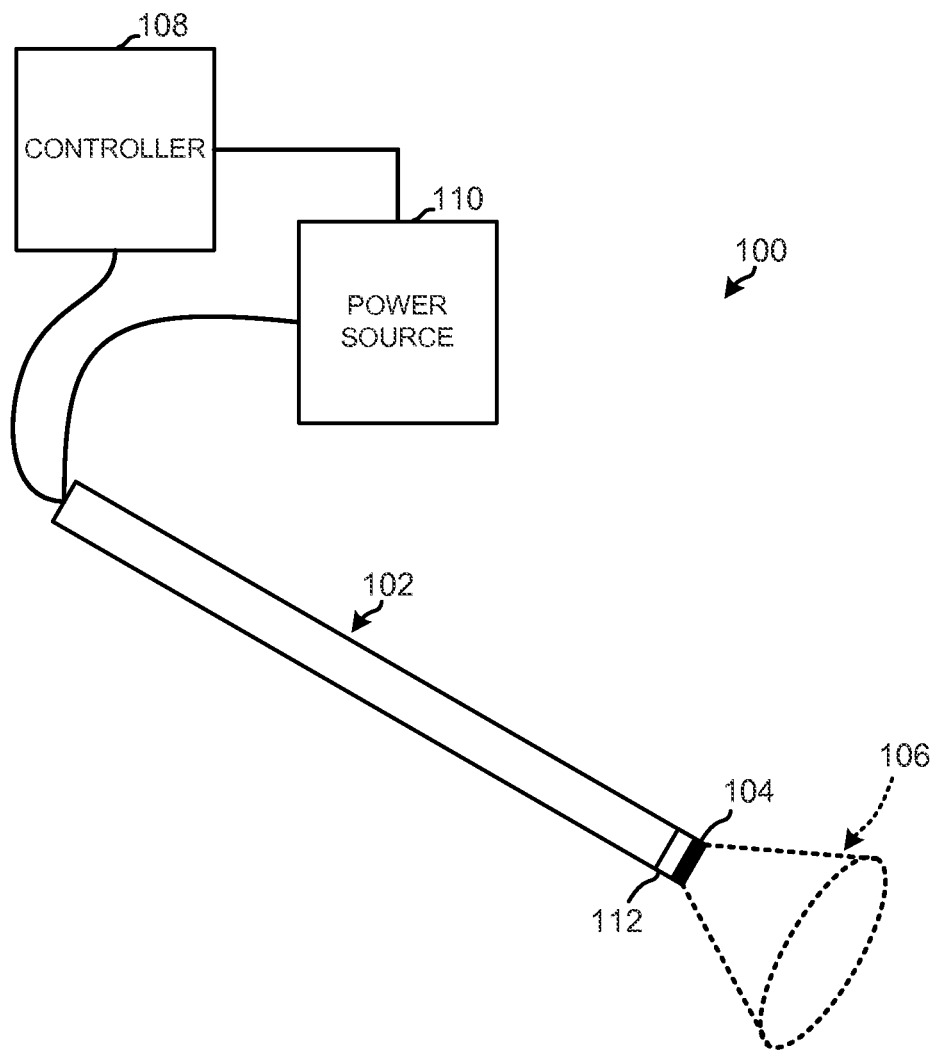
FIG. 1 illustrates a terahertz imaging system according to some embodiments of the present disclosure including a terahertz transceiver device positioned on a distal end of a cardiovascular catheter.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter). A "laser catheter" is a catheter that includes optical fibers capable of transmitting laser light.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The term "logic" or ""control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion on and/or in conjunction with computer-readable medium and would remain in accordance with the embodiments herein disclosed.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

A "laser emitter" refers to an end portion of a fiber or an optical component that emits laser light from a distal end of the catheter towards a desired target, which is typically tissue.

An optical fiber (or laser active fibre) is a flexible, transparent fiber made of an optically transmissive material, such as glass (silica) or plastic, which functions as a waveguide, or "light pipe", to transmit light between the two ends of the fiber.

The term "coordinated" and variations thereof refer to controlling multiple signals such that pulses based on the signals (for example, laser pulses and imaging pulses) are output at certain times relative to each other type of signal. For example, laser pulses based on corresponding laser activation signals and imaging pulses based on corresponding imaging activation signals may be output in synchronized non-overlapping time windows or in an asynchronous manner.

FIG. 1 illustrates a terahertz imaging system 100 according to some embodiments operative to produce 3D images of an intravascular space. Terahertz imaging system 100 includes a catheter 102, a terahertz transceiver 104 coupled to a distal end of catheter 102, a power source 110 providing power to terahertz transceiver 104, and a controller 108 in communication with power source 110 and transceiver 104. The distal end of catheter 102 is adapted for insertion into a lumen of a human including, for example, an intravascular space. Transceiver 104 is operative to generate and emit a terahertz signal in the form of terahertz radiation 106 directed towards a target area. Transceiver 104 also receives reflection signals or energy resulting from the terahertz energy emission and used by terahertz imaging system 100 for imaging the target area.

In some embodiments, terahertz transceiver 104 includes one or more integrated circuit chip devices, such as a silicon microchip. In one embodiment, transceiver 104 includes a complementary metal-oxide semiconductor (CMOS) microchip including a plurality of transistors cooperating to generate power for producing and emitting terahertz radiation. In one embodiment, the chip device of transceiver 104 includes multiple metal segments or other suitable antenna devices integrated onto the chip that are selectively operated (e.g., based on commands from controller 108) at a certain time and strength to radiate the terahertz signal in a particular direction and at a particular intensity.

Figure 2:
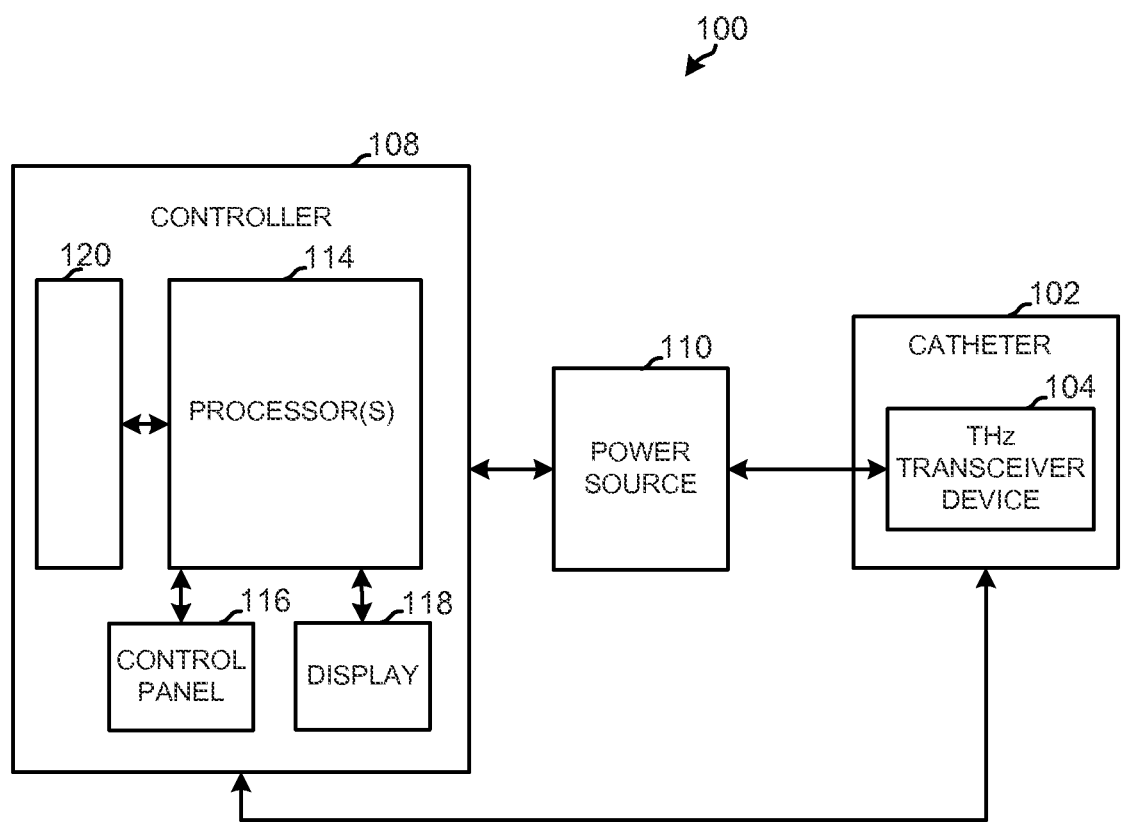
FIG. 2 illustrates a block diagram of the terahertz imaging system of FIG. 1.

Controller 108 includes one or more computing devices programmed to control terahertz transceiver 104 for scanning and capturing images of the lumen and tissue. Referring to FIG. 2, controller 108 includes a non-transitory computer-readable medium (e.g., memory 120) that includes instructions that, when executed, cause one or more processors 114 to control terahertz transceiver 104 and/or other components of terahertz imaging system 100. Controller 108 includes a control panel 116 having one or more user input devices, such as keys or buttons, for example, providing user control of terahertz imaging system 100. A display 118 includes a monitor or other display device for displaying images captured by terahertz imaging system 100 and other system data. In the illustrated embodiment, terahertz transceiver 104 is controlled to output the terahertz imaging signal (radiation 106) as a series of pulses.

Controller 108 is operative to control a direction of emission of the terahertz radiation 106 (FIG. 1). In some embodiments, controller 108 instructs transceiver 104 to emit radiation from particular metal segments integrated into the chip device of transceiver 104 to steer the beam of radiation 106 in a particular direction. The metal segments selected for emitting radiation may be dynamically changed to alter the direction of radiation 106. Further, in some embodiments catheter 102 further includes a movable end portion 112 at the distal end controllable by controller 108, as illustrated in FIG. 1. Transceiver 104 is coupled to movable end portion 112. Moveable end portion 112 is operative to rotate along one or more axes of rotation, for example about the x, y, and z axes of a Cartesian coordinate system. Controller 108 provides control signals to movable end portion 112 to change the orientation and direction of movable end portion 112 to thereby further steer the direction of radiation emission 106 by transceiver 104.

Controller 108 is further operative to control transceiver 104 and/or power source 110 to control the power intensity of terahertz radiation 106 output by transceiver 104. By varying the power intensity as well as the orientation and direction of the beam of terahertz radiation 106, terahertz imaging system 100 captures a contrast between different types of soft tissue. As such, terahertz imaging system 100 is operative to capture three-dimensional (3D) images of the lumen, tissue, and/or other target area of the human. Stated differently, when the transceiver 104 produces terahertz radiation 106 having a constant power intensity, the controller 108 creates a two-dimensional (2D) image for presentation on the display 118. When the transceiver 104 produces terahertz radiation 106 having a variable power intensity, the controller 108 creates a three-dimensional (3D) image for presentation on the display 118. The added dimension (i.e., $3^{rd}$ dimension) created by varying the transceiver's power production provides a clinician with a more complete visual representation of the lumen. Alternatively, the controller 108 may also vary the frequency of the terahertz radiation 106 to create a three-dimensional (3D) image for presentation on the display 118. The controller 108 may vary the frequency of the terahertz radiation 106 using a constant power intensity or a variable power intensity. Varying both the transceiver's power intensity and frequency of the terahertz radiation 106 may provide a clinician with an even more complete visual representation of the lumen.

Figure 3:
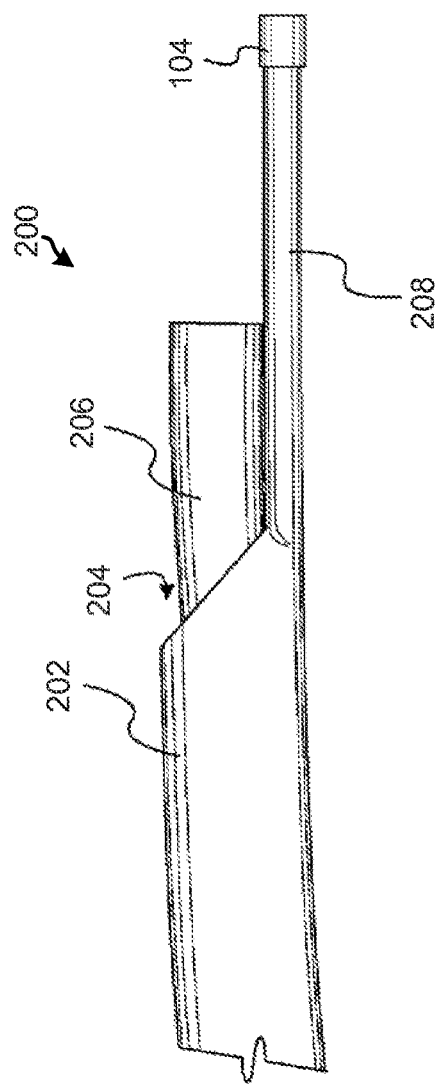
FIG. 3 illustrates an exemplary laser ablation catheter including a terahertz scanner.
Figure 4:
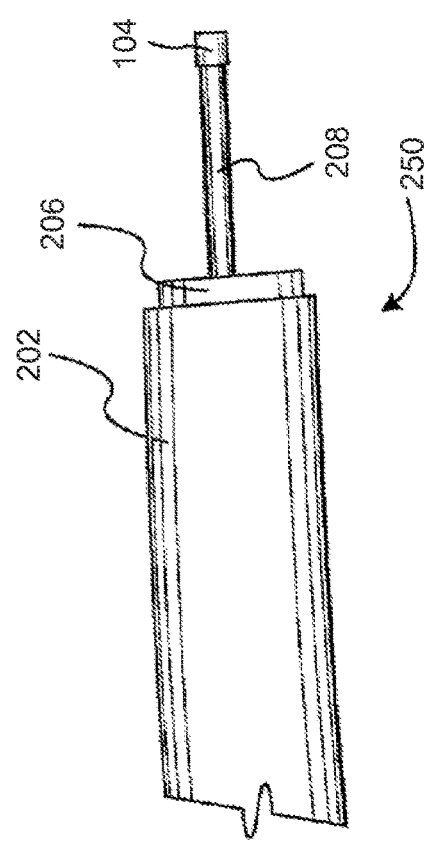
FIG. 4 illustrates another exemplary laser ablation catheter including a terahertz scanner.

In some embodiments, terahertz imaging system 100 is used prior to angioplasty or other intervention. In some embodiments, terahertz imaging system 100 is also used during and/or after an angioplasty or other intervention. For example, terahertz imaging system 100 may be used in conjunction with a laser ablation device. Exemplary catheters 102 of FIG. 1 that include both a laser ablation device and a terahertz imaging transceiver are illustrated in FIGS. 3 and 4. Referring to FIGS. 3 and 4, a catheter 200 (FIG. 3) and a catheter 250 (FIG. 4) each include a terahertz transceiver 104 at the distal end. Catheters 200 and 250 each illustratively include a catheter body 202 (or sheath) within which a fiber optic bundle 206 (or any other optical light guide) is disposed. Fiber optic bundle 206 includes any suitable number of optical fibers and, in some embodiments, includes a separate sheath. The optical fibers of bundle 206 serve as laser emitters at the distal end of bundle 206 by emitting pulsed laser energy to the targeted body lumen or tissue, such as a blood vessel, ureter, fallopian tube, cerebral artery. The pulsed laser energy serves to remove obstructions or other unwanted structures. The distal end of catheter body 202 includes an opening 204 from which the distal end of fiber optic bundle 206 extends. Transceiver 104 is coupled with one or more wires that extend through catheter body 202 toward the proximal end of catheter 200, 250 for coupling with power source 110 and controller 108 (FIG. 2).

Examples of laser catheters or laser sheath to which the terahertz transceiver 104 may be coupled include such laser catheters or laser sheaths sold by the Spectranetics Corporation under the tradenames ELCA™ and Turbo Elite™ (each of which is used for coronary intervention or catheterization such as recanalizing occluded arteries, changing lesion morphology, and facilitating stent placement) and SLSII™ and GlideLight™ (which is used for surgically implanted lead removal). The working (distal) end of a laser catheter typically has a plurality of laser emitters that emit energy and ablate the targeted tissue. The terahertz transceiver 104 may be coupled to this working end. The opposite (proximal) end of a laser catheter typically has a fiber optic coupler, which connects to a laser system or generator. One such example of a laser system is the CVX-300 Excimer Laser System, which is also sold by the Spectranetics Corporation.

The controller 108 and transceiver 104 may also be utilized in conjunction with mechanical lead extraction devices. An example of a mechanical lead extraction device is sold by the Spectranetics Corporation under the tradename TightRail™, which is a rotating mechanical dilator sheath used for lead removal. It may, therefore, be desirable to couple the transceiver 104 at, adjacent to or in the proximity of the distal end of the mechanical lead extraction device.

Continuing to refer to FIGS. 3 & 4, catheters 200 and 250 are each operative to couple to a laser apparatus to receive and conduct laser light provided by a laser source through bundle 206. In some embodiments, the laser apparatus includes an excimer laser or another suitable laser and produces light in the ultraviolet frequency range. Additional details of an exemplary laser apparatus are described in U.S. Pat. No. 5,383,199, filed Jul. 2, 1992, entitled "Apparatus and Method for Optically Controlling the Output Energy of a Pulsed Laser Source," the entire disclosure of which is incorporated by reference herein.

In the illustrated embodiments of FIGS. 3 and 4, transceiver 104 is disposed distal relative to the exit aperture of fiber optic bundle 206. In some embodiments, transceiver 104 is disposed on an eccentric or axially offset distal tip 208, as illustrated in FIG. 3. In other embodiments, transceiver 104 is disposed on an axially centered distal tip 208 positioned in fiber optic bundle 206, as illustrated in FIG. 4.

In some embodiments, the laser signals and terahertz imaging signals are each output as a plurality of pulses. Controller 108 of FIGS. 1 and 2 is operative to control or coordinate the pulsed laser and terahertz imaging outputs to reduce or eliminate signal interference.

Terahertz imaging system 100 provides high-resolution subsurface imaging. Terahertz imaging system 100 produces two and three-dimensional images of the target area such as the lumen, the arterial tissue, plaque, blockages, and/or tissue surrounding the artery. These images are generated in substantially real time and may be generated before, during, or after the laser operation. In the illustrated embodiment, terahertz radiation 106 is within the band of frequencies from 0.3 to 3 terahertz (THz). In some embodiments, terahertz radiation 106 is non-ionizing.

Additional examples of terahertz chip technology that may be utilized in terahertz transceiver 104 may be found in the article entitled "A 0.28 THz Power-Generation and Beam-Steering Array in CMOS Based on Distributed Active Radiators" by Kaushik Sengupta and Ali Hajimiri, published in IEEE Journal of Solid-State Circuits, Volume 47, Issue Number 12, date of publication December 2012, the entire disclosure of which is incorporated by reference herein.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A terahertz imaging system including:
   a catheter having a coupler configured to couple to a laser generator, the catheter operative to output laser energy to ablate an occlusion in a lumen of a human;
   a terahertz transceiver device coupled to the catheter, the terahertz transceiver device being operative to output terahertz radiation through the lumen and to receive reflection signals based on the terahertz radiation;
   a power source coupled to the terahertz transceiver device; and
   a controller in communication with the terahertz transceiver device, the controller being operative to coordinate output of laser energy and terahertz radiation to obtain an image of the lumen based on the reflection signals.

2. The terahertz imaging system of claim 1, wherein the terahertz transceiver device is coupled to a distal end of the catheter.

3. The terahertz imaging system of claim 1, wherein the controller is operative to control a direction of the terahertz radiation emitted by the terahertz transceiver device.

4. The terahertz imaging system of claim 3, wherein the catheter includes a movable end portion controlled by the controller, the terahertz transceiver device is coupled to the movable end portion of the catheter, and the controller is operative to control movement of the movable end portion of the catheter to control the direction of the terahertz radiation emitted by the terahertz transceiver device.

5. The terahertz imaging system of claim 1, wherein the controller is operative to control a power intensity of the terahertz radiation emitted by the terahertz transceiver device.

6. The terahertz imaging system of claim 1, wherein the controller varies the power intensity of the terahertz radiation emitted by the terahertz transceiver device.

7. The terahertz imaging system of claim 6, wherein the controller is operative to control frequency of the terahertz radiation emitted by the terahertz transceiver device.

8. The terahertz imaging system of claim 1, wherein the image obtained by the controller is a three-dimensional (3D) image.

9. The terahertz imaging system of claim 1, further comprising a laser delivery device including a fiber optic bundle.

10. A terahertz imaging method including:
    providing a catheter, a terahertz transceiver device coupled to the catheter, a power source for the terahertz transceiver, and a laser source coupled to the catheter;
    activating the power source to deliver terahertz radiation from the power source to the terahertz transceiver device;
    emitting the terahertz radiation from the terahertz transceiver device through a lumen of a human;
    receiving reflection signals based on the terahertz radiation;
    obtaining an image of the lumen based on the reflection signals; and
    coordinating the emission of a laser signal from the catheter to ablate an occlusion in the lumen.

11. The terahertz imaging method of claim 10, further including controlling a direction of the terahertz radiation emitted by the terahertz transceiver device.

12. The terahertz imaging method of claim 10, further including controlling a power intensity of the terahertz radiation emitted by the terahertz transceiver device.

13. The terahertz imaging method of claim 10, wherein the image of the lumen based on the reflection signals is a three-dimensional (3D) image.

14. A non-transitory computer-readable medium containing instructions that, when executed, cause one or more processors to perform a method including:

activating a power source to deliver terahertz radiation from the power source to a terahertz transceiver device coupled to a catheter;

emitting the terahertz radiation from the terahertz transceiver device through a lumen of a human;

emitting a laser signal from the laser delivery device to ablate an occlusion in the lumen;

receiving reflection signals based on the terahertz radiation;

obtaining an image of the lumen based on the reflection signals; and coordinating emission of the laser signal and the terahertz radiation.

15. The non-transitory computer-readable medium of claim 14, the method further including controlling a direction of the terahertz radiation emitted by the terahertz transceiver device.

16. The non-transitory computer-readable medium of claim 15, the method further including controlling movement of an end portion of the catheter to control the direction of the terahertz radiation emitted by the terahertz transceiver device.

17. The method of claim 14, further including controlling frequency of the terahertz radiation emitted by the terahertz transceiver device.

* * * * *